US009492658B2

(12) United States Patent
Shireman et al.

(10) Patent No.: US 9,492,658 B2
(45) Date of Patent: Nov. 15, 2016

(54) GUIDE CATHETER OCCLUSION BALLOON WITH ACTIVE INFLATION

(71) Applicant: Cardiac Pacemakers, Inc., St. Paul, MN (US)

(72) Inventors: Brice L. Shireman, Maple Grove, MN (US); Brian R. Reynolds, Ramsey, MN (US); Bruce A. Tockman, Scandia, MN (US); Pu Zhou, Irvine, CA (US); Henry J. Pepin, Loretto, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 462 days.

(21) Appl. No.: 14/079,861

(22) Filed: Nov. 14, 2013

(65) Prior Publication Data
US 2014/0135789 A1    May 15, 2014

Related U.S. Application Data

(60) Provisional application No. 61/727,006, filed on Nov. 15, 2012.

(51) Int. Cl.
*A61B 19/00*        (2006.01)
*A61N 1/05*         (2006.01)
(Continued)

(52) U.S. Cl.
CPC ............ *A61N 1/056* (2013.01); *A61M 25/005* (2013.01); *A61M 25/0026* (2013.01);
(Continued)

(58) Field of Classification Search
CPC ................... A61M 25/005; A61M 2025/1052; A61M 2025/0034; A61M 2025/1061; A61M 25/0045; A61M 2025/0036; A61M 2025/0039; A61M 2025/004; A61M 2025/0047; A61M 2025/0059; A61M 2025/1088; A61M 25/0026; A61M 25/0032; A61M 25/0043; A61M 25/0053; A61M 25/0054; A61M 25/0662

USPC ........ 604/96.01, 508; 600/18; 606/129, 191, 606/194, 198, 200
See application file for complete search history.

(56) References Cited

U.S. PATENT DOCUMENTS 5,156,594 A  * 10/1992  Keith ................ A61M 25/0662
                                                      604/103.09
5,328,472 A  *  7/1994  Steinke ............... A61M 25/104
                                                      604/102.02

(Continued)

FOREIGN PATENT DOCUMENTS

EP        0709108 B1    5/1996
JP      2006516451 A    7/2006
(Continued)

OTHER PUBLICATIONS

MicroLumen. "Polyimide Tubing: Dispelling the Myths". May 29, 2008    <http://www.microlumen.com/news/industry-news/18-polyimide-tubing-dispelling-the-myths>.*

(Continued)

*Primary Examiner* — Katherine M Shi
(74) *Attorney, Agent, or Firm* — Faegre Baker Daniels LLP

(57) ABSTRACT

Various embodiments concern a guide catheter for delivery of an implantable lead within the coronary vein. Such a guide catheter can comprise a tubular body having a main lumen and at least one preformed bend. The tubular body can comprise a liner defining an inner surface, braiding circumferentially surrounding the liner, a jacket covering the braiding and defining an exterior surface of the tubular body, and a plurality of inflation tubes embedded within the jacket. The guide catheter can include a balloon mounted on the tubular body, each of the plurality of inflation tubes in communication with the balloon. The guide catheter can further include a hub providing access to the main lumen, the hub comprising a first port for introduction of contrast media into the main lumen and a second port in communication with the plurality of inflation tubes.

12 Claims, 7 Drawing Sheets

(51) Int. Cl.
  *A61M 25/10* (2013.01)
  *A61M 25/00* (2006.01)
  *A61M 25/06* (2006.01)

(52) U.S. Cl.
  CPC .... *A61M 25/0045* (2013.01); *A61M 25/0662* (2013.01); *A61M 25/1002* (2013.01); *A61M 25/1034* (2013.01); *A61M 25/1036* (2013.01); *A61M 2025/0047* (2013.01); *A61M 2025/1052* (2013.01); *A61M 2025/1061* (2013.01); *Y10T 29/49885* (2015.01)

(56) References Cited

U.S. PATENT DOCUMENTS

| | | | |
|---|---|---|---|
| 5,628,754 A | 5/1997 | Lunn et al. | |
| 5,743,875 A * | 4/1998 | Sirhan | A61L 29/041 604/524 |
| 5,755,687 A | 5/1998 | Donlon | |
| 5,800,486 A * | 9/1998 | Thome | A61B 18/18 607/101 |
| 5,891,090 A * | 4/1999 | Thornton | A61M 25/0052 604/103.09 |
| 5,928,181 A | 7/1999 | Coleman et al. | |
| 6,022,336 A * | 2/2000 | Zadno-Azizi | A61B 17/22 604/101.05 |
| 6,129,737 A * | 10/2000 | Hamilton | A61M 25/1002 604/916 |
| 7,935,075 B2 | 5/2011 | Tockman et al. | |
| 2002/0026145 A1* | 2/2002 | Bagaoisan | A61M 25/0009 604/96.01 |
| 2002/0198492 A1* | 12/2002 | Miller | A61M 25/0053 604/96.01 |
| 2012/0150107 A1* | 6/2012 | Cheung | A61B 5/6853 604/96.01 |
| 2013/0253417 A1* | 9/2013 | Dinh | A61M 25/0012 604/28 |

FOREIGN PATENT DOCUMENTS

| | | |
|---|---|---|
| JP | 2008092969 A | 4/2008 |
| WO | WO9839046 A1 | 9/1998 |
| WO | 2004067078 A2 | 8/2004 |

OTHER PUBLICATIONS

International Preliminary Examination Report issued in PCT/US2013/070031, mailed May 19, 2015, 10 pages.
International Search Report and Written Opinion issued in PCT/US2013/070031, mailed Feb. 2, 2014, 15 pgs.

* cited by examiner

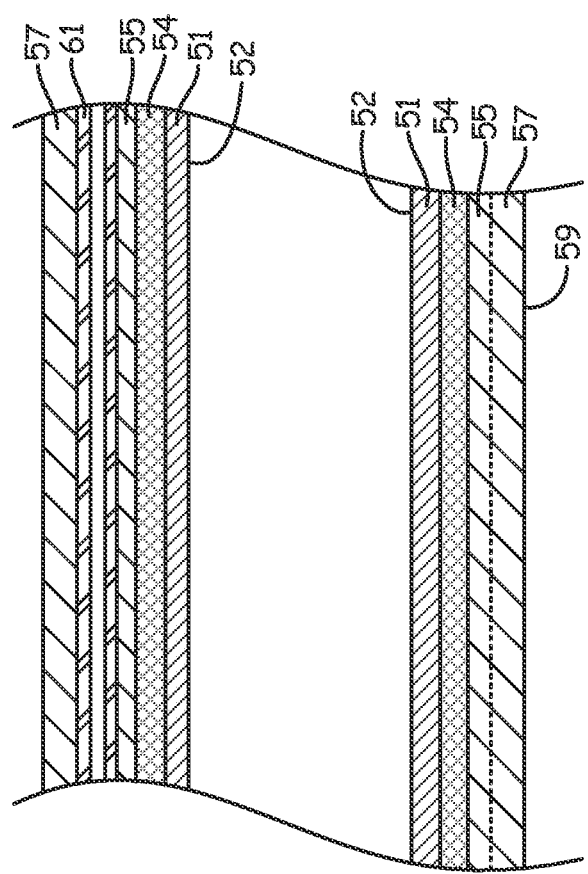
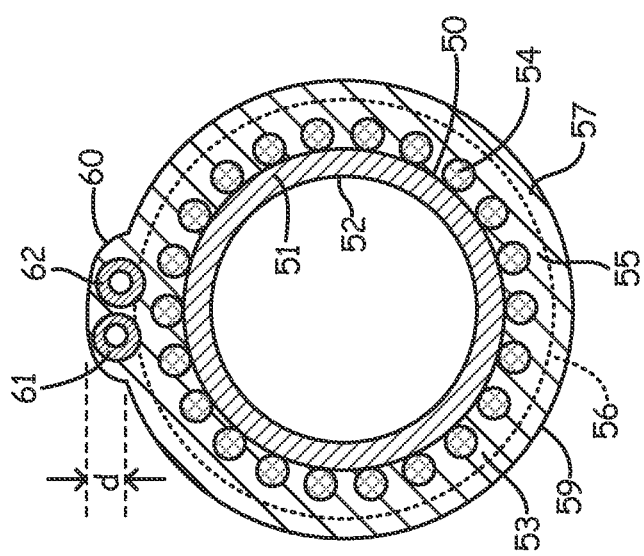

GUIDE CATHETER OCCLUSION BALLOON WITH ACTIVE INFLATION

CROSS-REFERENCE TO RELATED APPLICATION

This application claims priority to U.S. Provisional Application No. 61/727,006, filed Nov. 15, 2012, which is herein incorporated by reference in its entirety.

TECHNICAL FIELD

The present disclosure relates to medical devices and methods for accessing anatomical spaces in the body. More specifically, various embodiments concern a guide catheter for delivering an implantable lead in a vessel, the guide catheter having a balloon that at least partially blocks blood flow to obtain a venogram.

BACKGROUND

Cardiac rhythm management systems are used to treat arrhythmias and other abnormal heart conditions. Such systems generally include one or more cardiac leads implanted in or about the heart for delivering electrical stimulation to cardiac tissue and/or sensing electrical signals from cardiac tissue.

The left ventricle can be targeted for electrical stimulation in cardiac resynchronization therapy. A lead implanted within the vasculature along the left ventricle can deliver electrical stimulation to the left ventricle. Ideally, the lead is accurately implanted in an efficient procedure with a minimum number of steps. As such, there is a continuing need in the art for a device adapted to facilitate the accurate and efficient placement of a lead in a location suitable for stimulation of the left ventricle.

SUMMARY

Example 1 concerns a guide catheter for delivery of an implantable lead, the guide catheter comprising: a tubular body having a proximal end, a distal end, and a main lumen that extends from the proximal end to the distal end, the main lumen dimensioned to allow the implantable lead to move within the main lumen, the tubular body comprising: a jacket defining an exterior surface of the tubular body; and a plurality of inflation tubes embedded within the jacket; a balloon mounted on the distal end of the tubular body, each of the plurality of inflation tubes in communication with the balloon, the balloon inflatable to at least partially occlude the coronary vein of the heart; and a hub mounted on the proximal end of the tubular body, the hub providing access to the main lumen and the plurality of inflation tubes.

In example 2, the guide catheter of example 1, wherein: an inner surface of the main lumen is defined by a liner formed from a first type of polymer material, and the jacket is formed from a second type of polymer material.

In example 3, the guide catheter of example 2, wherein the tubular body further comprises braiding circumferentially surrounding the liner, and the braiding is covered by the jacket.

In example 4, the guide catheter of any of examples 1-3, wherein: the jacket is formed from a second type of polymer material, the plurality of inflation tubes are formed from a third type of polymer material, and the second type of polymer material is different than the third type of polymer material.

In example 5, the guide catheter of examples 4, wherein the third type of polymer material has a higher melting temperature than the second type of polymer material.

In example 6, the guide catheter of example 4, wherein the jacket comprises: a first layer of the second type of polymer material underneath the plurality of inflation tubes, and a second layer of the second type of polymer material disposed radially over the plurality of inflation tubes and bonded to the first layer.

In example 7, the guide catheter of any of examples 1-6, wherein an outer circumferential profile of the tubular body has a bump and the plurality of inflation tubes extend underneath the bump along the tubular body.

In example 8, the guide catheter of example 7, wherein the plurality of inflation tubes extend adjacent to one another along the tubular body.

In example 9, the guide catheter of any of examples 1-8, wherein the plurality of inflation tubes have greater kink resistance than the tubular body.

In example 10, the guide catheter of any of examples 1-9, wherein the balloon has a blunted distal end profile when inflated that deflects retrograde blood flow in the coronary vein and a tapered proximal end profile that minimizes a retraction force necessary to pull the balloon into a sheath when the balloon is at least partially inflated.

Example 11 concerns a guide catheter for delivery of an implantable lead, the guide catheter comprising: a tubular body having a proximal end, a distal end, a main lumen that extends from the proximal end to the distal end, and an outer cross-sectional profile, the main lumen dimensioned to allow the implantable lead to move within the main lumen, the tubular body comprising: a liner defining an inner surface of the main lumen, the liner formed from a first type of polymer material; a jacket defining an exterior surface of the tubular body, the jacket formed from a second type of polymer material; and at least one inflation tube embedded within the jacket, the at least one inflation tube extending from the proximal end to the distal end, the at least one inflation tube formed from a third type of polymer material, wherein each of the at least one inflation tube is more kink resistant than the tubular body, the second type of polymer material is different than the third type of polymer material, and the outer cross-sectional profile of the tubular body has a bump that extends over the at least one inflation tube along the tubular body; and a balloon mounted on the distal end of the tubular body, the at least one inflation tube in communication with the balloon, the balloon inflatable to at least partially occlude the coronary vein of the heart.

In example 12, the guide catheter of example 11, wherein the balloon has a blunted distal end profile when inflated that deflects retrograde blood flow in the coronary vein and a tapered proximal end profile that minimizes a retraction force necessary to pull the balloon into a sheath when the balloon is at least partially inflated.

In example 13, the guide catheter of either of examples 11 or 12, wherein the jacket comprises: a first layer of the second type of polymer material underneath the at least one inflation tube and at least partially encapsulating the braiding, and a second layer of the second type of polymer material disposed radially over the at least one inflation tube and bonded to the first layer, the bump in the outer cross-sectional profile of the tubular body at least partially formed by the second layer.

In example 14, the guide catheter of any of examples 11-13, wherein each of the at least one inflation tube is more kink resistant than the tubular body based at least in part on the at least one inflation tube having a higher elongation characteristic than the tubular body.

Example 15 concerns a method of making a guide catheter, the method comprising: forming a tubular body, the tubular body having a proximal end, a distal end, and a main lumen extending from the proximal end to the distal end, the tubular body formed by: extending braiding over a polymer tube, the polymer tube formed from a first type of polymer material; applying a first layer of a second type of polymer material over the braiding and the polymer tube; placing at least one inflation tube along an exterior surface of the first layer, the at least one inflation tube being formed from a third type of polymer material that is different from the second type of polymer material; and applying a second layer of the second type of polymer material over the first layer and the at least one inflation tube, wherein heat is applied during the application of the second layer to bond the second layer to the first layer and embed the at least one inflation tube between the first layer and the second layer; and attaching a balloon to the tubular body over a distal tip of each of the at least one inflation tube such that the balloon can be inflated and deflated via the at least one inflation tube.

In example 16, the method of example 15, wherein the melting temperature of the third type of polymer material is greater than the melting temperature of the second type of polymer material.

In example 17, the method of example 16, wherein applying the second layer comprises heating the second layer to a temperature that is about equal to the melting temperature of the second type of polymer material but below the melting temperature of the third type of polymer material.

In example 18, the method of any of examples 15-17, wherein: the at least one inflation tube contains beading when the at least one inflation tube is placed along the exterior surface of the first layer, and the beading is removed from the at least one inflation tube after the second layer is applied over the first layer and the at least one inflation tube.

In example 19, the method of any of examples 15-18, wherein: placing the at least one inflation tube along the exterior surface of the first layer comprises placing at least two inflation tubes along the exterior surface of the first layer, applying the second layer comprises applying the second layer over the at least two inflation tubes, and attaching the balloon comprises attaching the balloon to the tubular body over each distal tip of the at least two inflation tubes such that the balloon can be inflated and deflated via the lumens of the at least two inflation tubes.

In example 20, the method of any of examples 15-19, wherein applying the second layer comprises: placing a tube formed from the second type of polymer material over the first layer and the at least one inflation tube, placing a heat shrink tube formed from a fourth type of polymer material over the tube formed from the second type of polymer material, applying heat along the heat shrink tube to cause the second type of polymer material of the tube to bond with the second type of polymer material of the first layer, and removing the heat shrink tube from over the tubular body.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIGS. 4A-B illustrates cross-sectional views of a guide catheter.

Figure 1:
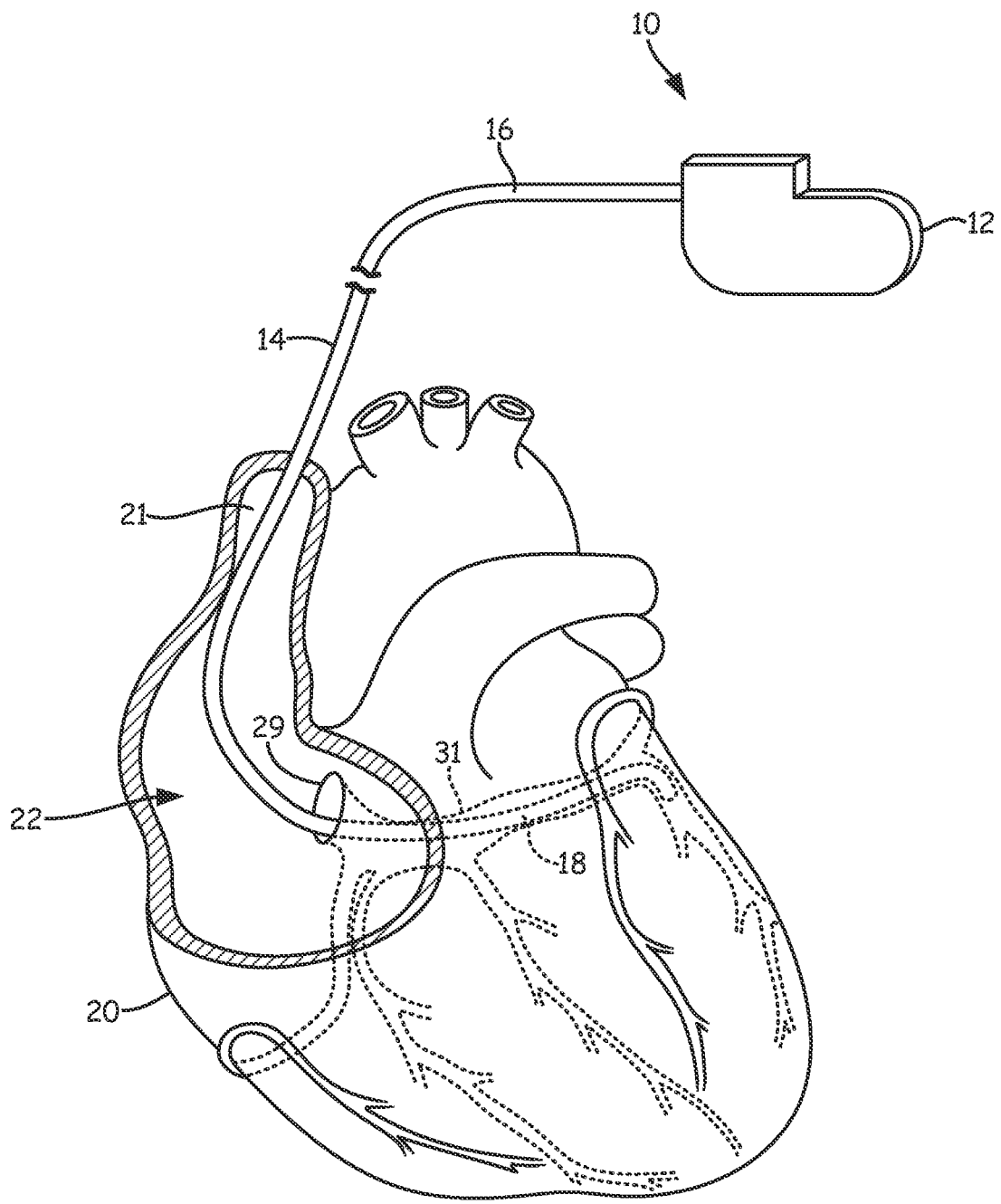
FIG. 1 illustrates a cardiac lead implanted in the vicinity of the coronary sinus.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a schematic drawing of a cardiac rhythm management system 10 including a pulse generator 12 coupled to a lead 14 having a proximal end 16 and a distal end 18. The lead 14 can enter the vascular system through a vascular entry site formed in the wall of the left subclavian vein (not illustrated) and extend through the left brachiocephalic vein (not illustrated) and the superior vena cava 21 to access the patient's heart 20. The distal end 18 of the lead 14 can extend through the right atrium 22, through the coronary sinus ostium 29, and into the coronary sinus 31. The illustrated position of the lead 14 may be used for sensing, delivering pacing pulses, and/or delivering defibrillation energy to the left side of the heart 20 for the treatment of arrhythmias or other cardiac disorders. A pulse generator 12, to which the lead 14 can be connected, can be implanted within a pocket formed in the patient's chest or abdomen. The lead 14 can be delivered into the coronary sinus 31 with a guide catheter, as further discussed herein.

Figure 2:
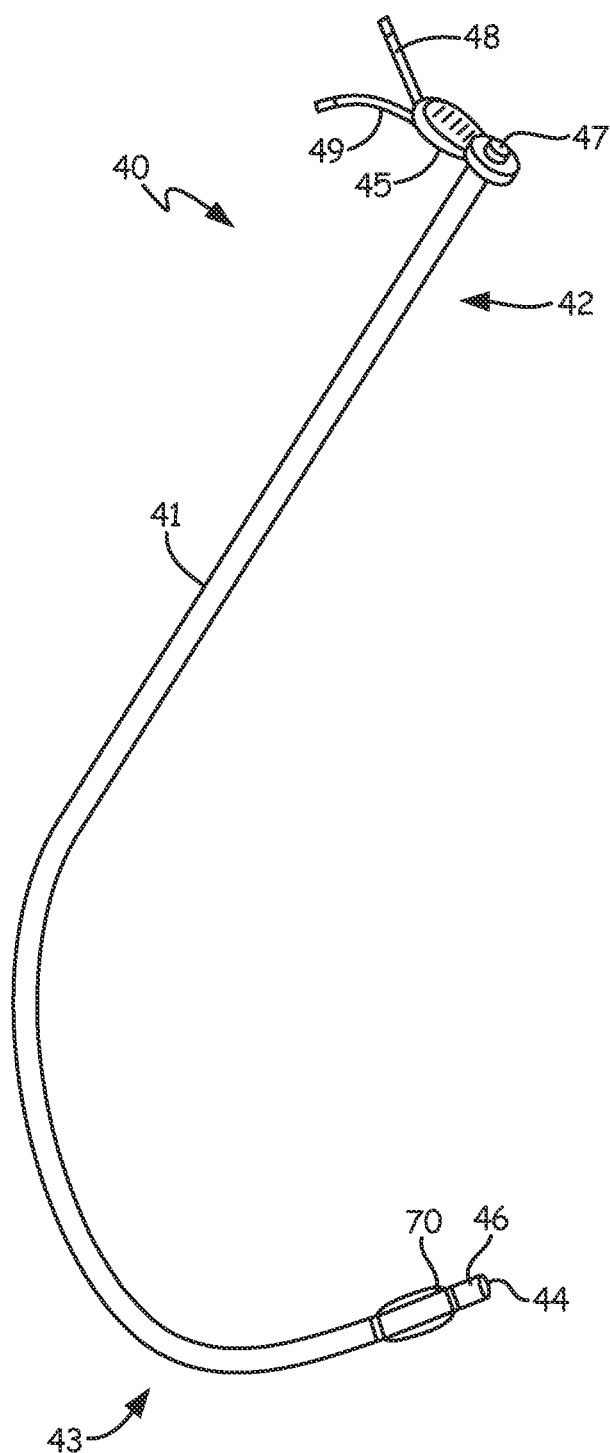
FIG. 2 illustrates a guide catheter for implanting a lead through the coronary sinus.

FIG. 2 illustrates a schematic diagram of a guide catheter 40. The guide catheter 40 can include a tubular body 41, a proximal end 42, and a distal end 43. The tubular body 41 can include a main lumen that extends the entire length of the tubular body 41. The main lumen can have an opening 44 at the distal tip 46. The main lumen can be accessible through a main port 47 of a hub 45. The hub 45 can include a handle 45, an inflation port 48, and a contrast medium port 49. The distal tip 46 of the guide catheter 40 can comprise a polymer containing tungsten to allow the distal tip 46 to be radiopaque.

Figure 3:
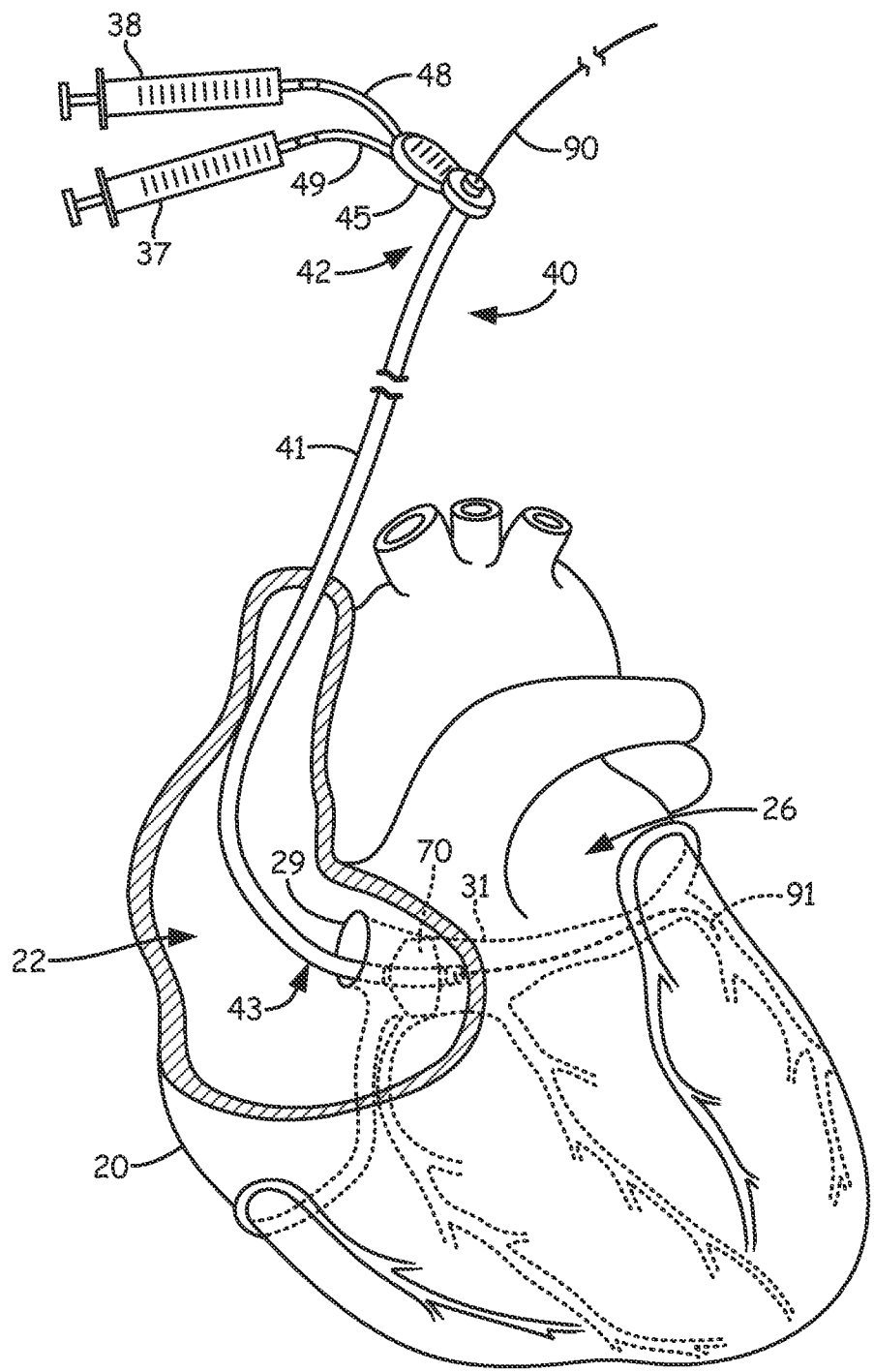
FIG. 3 illustrates a guide catheter cannulating and partially occluding the coronary sinus.

FIG. 3 illustrates the guide catheter 40 cannulating the coronary sinus 31. A distal end 91 of a guide wire 90 can extend distally from the main lumen of the guide catheter 40 into a branching vessel. The inflation port 48 can interface with a second syringe 38 or other device for introducing a fluid into the guide catheter 40. The inflation port 48 can be in communication with one or more inflation tubes that can extend along the tubular body 41 to a balloon 70 of the distal end 43 of the guide catheter 40. The balloon 70 can be inflated by the fluid provided by the first syringe 38 connected to inflation port 48. The balloon 70 can be inflated to at least partially occlude the coronary sinus 31.

The contrast medium port 49 can interface with a second syringe 37 or other device for introducing contrast media (e.g., iodine perceivable in venographic imaging by an X-ray device). The contrast medium port 49 can be in communication with the main lumen and/or a contrast medium lumen of the guide catheter 40 for routing contrast media through the guide catheter 40 and into the coronary sinus 31 and branching vessels. The contrast media may exit the distal opening 44 of the main lumen in various embodiments. The introduction of contrast media as part of a venogram procedure can allow visualization of the branching vessels, distal of the distal opening 44, to facilitate accurate placement of the lead 14. However, the branching vessels representing possible implant sites are generally upstream relative to the coronary sinus 31 where the contrast media is injected. Accordingly, the movement of the contrast media may need to be retrograde to the normal blood flow within the coronary sinus 31. In order to facilitate the flow of contrast media to possible implant sites, the balloon 70 can be inflated to partially or fully block the blood flow within the coronary sinus 31 to allow the contrast media to travel into the branching vessels for visualization of the branching vessels.

FIGS. 4A-B illustrate cross-sectional diagrams of the tubular body 41. FIGS. 4A-B show that the tubular body 41 comprises a main lumen 50 defined by the inner surface 52 of a liner 51. In some embodiments, the liner 51 is an elongated tube that extends the entire length of the tubular body 41. The main lumen 50 can be dimensioned to allow a lead to be advanced within the main lumen 50. For example, the inner diameter of the main lumen 50 can be about 0.065-0.105 inches. In some embodiments, the liner 51 can be formed from a first type of polymer material. The first type of polymer material can be a lubricious or an otherwise low friction material to minimize friction between the inner surface 52 of the main lumen 50 and the lead body during advancement of the lead 14. In various embodiments, the first type of polymer material is polytetraflouroethelyne (PTFE). In various embodiments, the liner 51 has an outer diameter of about 0.067-0.107 inches. In various embodiments, the liner 51 can have a wall thickness of about 0.001 inches.

In various embodiments, the tubular body 41 can include a layer of braiding 54 radially outward from, and adjacent to, the liner 51. As shown in FIG. 4A, the braiding 54 can circumferentially surround the liner 51. The braiding 54 can be a braid of stainless steel wires, although other materials could additionally or alternatively be used. The braiding 54 can stiffen the tubular body 41 to facilitate the transfer of torque along the tubular body 41 and/or resist kinking of the tubular body 41. In some embodiments, the braiding 54 can extend the entire length of the tubular body 41. In some other embodiments, the braiding 54 may not extend to a distal tip 46 or other distal portion of the guide catheter 40, allowing one or more distal portions of the guide catheter 40 to be more flexible relative to one or more proximal portions that include the braiding 54. In some embodiments, the individual braid wires can have a diameter of about 0.004 inches. It is noted that not all embodiments may include the liner 51 and/or the braiding 54.

The tubular body 41 can further include a jacket 53 covering the braiding 54. The tubular body 41 can define an exterior surface 59 of the tubular body 41. The jacket 53 can comprise multiple layers of polymer material. As shown in FIG. 4A, the jacket 53 can comprise a first layer 55 of polymer material and a second layer 57 of polymer material. Each of the first layer 55 and the second layer 57 can be formed from a second type of polymer material, as compared to the first type of polymer material used to form the liner 51. In various embodiments, the second type of polymer material can be polyether block amide (PEBA). In embodiments where the first layer 55 and the second layer 57 are each formed from the same type of polymer material, the first layer 55 can be bonded together along the length of the tubular body 41. Reference line 56 is provided to graphically demarcate the first layer 55 and the second layer 57, however the polymer material can be continuous and uniform between the first layer 55 and the second layer 57. For example, the first layer 55 and the second layer 57 can be seamlessly bonded to each other to form the jacket 53. While the first layer 55 and the second layer 57 can be formed from the same type of polymer material, in some embodiments, the first layer 55 and the second layer 57 can be formed from different types of polymer material In some embodiments, the first layer 55 can at least partially encapsulate the braiding 54 to mechanically connect the braiding 54 and the jacket 53. In some embodiments, the jacket 53 can extend the entire length of the tubular body 41. In some embodiments, the first layer 55 and the second layer 57 can extend for the entire length of the tubular body 41. However, in some other embodiments, only the first layer 55 may extend the entire length of the tubular body 41 while the second layer 57 may extend for less than the entire length of the tubular body 41. For example, in some embodiments the second layer 57 may not extend to the balloon 70, or may overlap with part of the balloon 70 but not extend distally of the balloon 70.

The use of multiple layers of polymer material to form the jacket 53 can embed one or more inflation tubes within the jacket 53. FIG. 4A shows a first inflation tube 61 and a second inflation tube 62 embedded in the jacket 53. Specifically, the first inflation tube 61 and the second inflation tube 62 each lie between the first layer 55 and the second layer 57 of the jacket 53 as indicated by reference line 56. In some embodiments, the first inflation tube 61 and the second inflation tube 62 are aligned with the longitudinal axis of the tubular body 41 such that each inflation tube extends straight along the tubular body 41 between the hub 45 and the balloon 70. In some embodiments, the first inflation tube 61 and the second inflation tube 62 can be wound within the jacket 53 such that each inflation tube spirals around the tubular body 41.

The first inflation tube 61 and the second inflation tube 62 can each be formed from a third type of polymer material. The third type of polymer material can be a different type than the second type of polymer material that forms the first layer 55 and the second layer 57 of the jacket 53. For example, the first inflation tube 61 and the second inflation tube 62 can be formed from PTFE while the first layer 55 and the second layer 57 of the jacket 53 can be formed from PEBA. Alternatively, the first inflation tube 61 and the second inflation tube 62 can be formed from FEP. The exterior surfaces of the first inflation tube 61 and the second inflation tube 62 can be chemically etched to facilitate bonding between the third type of polymer material of the first inflation tube 61 and the second inflation tube 62 and the second type of polymer material of the jacket 53. While FIG. 4A shows two inflation tubes embedded between the layers of the jacket 53, a single inflation tube, three inflation tubes, or a greater number of inflation tubes can be embedded between the layers of the jacket 53 in various embodiments.

In some embodiments, the first inflation tube 61 and the second inflation tube 62 can form part of a communication circuit between the inflation port 48 and the balloon 70, described herein with respect to FIG. 3. As such, fluid introduced into the inflation port 48 can pressurize the first inflation tube 61, the second inflation tube 62, and the balloon 70 to partially or fully inflate the balloon 70. The communication circuit between the inflation port 48 and the balloon 70 can be sealed such that pressure can be maintained as long as desired without introducing more fluid from the inflation port 48. In some embodiments, either of the first inflation tube 61 or the second inflation tube 62 can have an elongate metal member extending within the tube lumen. Alternatively, either of the first inflation tube 61 or the second inflation tube 62 can be replaced by an elongate metal member. The elongate metal member can provide crush resistance to an adjacent and open inflation tube, such that at least one inflation tube can be maintained in an open configuration during kinking or compression of the tubular body 41.

In various embodiments, the guide catheter 40 can have multi-functionality in that it can partially or fully occlude the coronary sinus 31 with the balloon 70 to allow a venogram to be taken while also guiding the advancement of a lead within the main lumen 50. The multi-functionality of the guide catheter 40 may allow the guide catheter 40 to replace multiple catheters and additional procedural steps that may otherwise be used in a lead implantation procedure.

For example, conventionally, a small catheter having an occlusion balloon and a lumen for the introduction of contrast media can be used to obtain a venogram. The small catheter can then be withdrawn and replaced by a larger conventional guide catheter lacking a balloon but large enough to accommodate a lead. However, expanding the lumen of the conventional venography catheter to accommodate a lead, or adding a balloon and inflation lumen to the conventional guide catheter, may expand the outer profile of either catheter to a size too large to cannulate the coronary sinus 31. Embodiments of the present disclosure minimize the profile of the guide catheter 40 by including various features discussed herein, such as the use of multiple inflation tubes and/or embedding the inflation tubes between different layers of a jacket The inflation pressure needed to be developed to inflate and deflate a balloon is inversely related to the interior cross-sectional area of the inflation tube in communication with the balloon. It can be noted that having a large interior cross-sectional area can be used to facilitate balloon deflation because the vacuum created can pull the inflation tube walls inward, shrinking the cross-sectional area and slowing the deflation process. For example, in some cases it can take ten times as long to deflate a balloon as compared to the inflation time. However, the time to deflate an occlusion balloon is ideally minimized to shorten the time during which blood flow in the heart is blocked and to allow quick removal of a guide catheter in case a problem is encountered.

Multiple inflation tubes can be provided in various embodiments of the present disclosure to divide out the total cross sectional area needed to inflate and deflate the balloon 70. Multiple inflation lumens can have a lower height as compared to a single inflation lumen with the same total cross-sectional area. The first inflation tube 61 and the second inflation tube 62 are shown in FIG. 4A below the bump 60 in the exterior surface 59 of the jacket 53. The bump 60 increases the outer profile of the tubular body 41 by a distance "d" as compared to the exterior surface 59 without the bump 60. In some embodiments, "d" is about 0.007 inches. The distance "d" would be greater if the first inflation tube 61 and the second inflation tube 62 were replaced by a single inflation tube having the same total lumen cross-sectional area. Accordingly, the outer profile of the exterior surface 59 of the tubular body 41 can be minimized by dividing the inflation of the balloon 70 between the first inflation tube 61 and the second inflation tube 62 (or other number of inflation tubes).

At least partially accommodating the first inflation tube 61 and the second inflation tube 62 within the bump 60, and having all of the first inflation tube 61 and the second inflation tube 62 within one bump 60, can allow a minimal expansion of the outer profile of the tubular body 41 as compared to inflation lumens being built into a wall of a catheter. If a conventional inflation lumen was built into the catheter wall (e.g., by extrusion), the radius of the tubular body 41 would be increased by a distance "d" circumferentially around the tubular body 41. The bump 60 can be limited in width and profile as compared to increasing the radius of the entire circumference of the tubular body 41 to the same radius as the bump 60. Because the first inflation tube 61 and the second inflation tube 62 can be added to the tubular body 41 while increasing the outer profile only a small amount along the bump 60, the tubular body 41 can essentially be the same size as a conventional guide catheter (e.g., about 9 French) but allow for inflation of the balloon 70 to perform a venogram.

Embedding one or more inflation tubes between layers of a jacket, as described herein, can have particular advantages. Conventionally, a collapsed or otherwise blocked inflation tube can present particular problems if the inflation tube collapses while a balloon is inflated. A catheter may become stuck in a vessel because the catheter cannot physically be removed with the balloon in the inflated state and yet the balloon may not deflate because the inflation lumen is collapsed or otherwise obstructed.

Various features are disclosed herein to avoid collapsing or facilitate quick recovery of the first inflation tube 61 and the second inflation tube 62. In some embodiments, the first inflation tube 61 and the second inflation tube 62 can be configured to be less likely to kink than the tubular body 41. In such embodiments, kinking of the tubular body 41 may not lead to kinking of the first inflation tube 61 and the second inflation tube 62 as the first inflation tube 61 and the second inflation tube 62 may still be able to curve along the bend of the kink of the larger tubular body 41. A user may be less likely to cause the first inflation tube 61 and the second inflation tube 62 to kink if the tubular body 41 is more likely to kink (e.g., for some situations, the user is likely to have already kinked and withdrawn the tubular body 41 before being able to get the guide catheter 40 in a position that would kink the first inflation tube 61). Various features can be provided to make the first inflation tube 61 and the second inflation tube 62 more kink resistant than the tubular body 41. For example, the first inflation tube 61 and the second inflation tube 62 can have a higher elongation characteristic than the tubular body 41. The elongation characteristic can be a yield strain limit. In some embodiments, each of the first inflation tube 61 and the second inflation tube 62 can have a ratio between the wall thickness of the inflation tube and the outer diameter of the inflation tube (i.e. a wall thickness-to-outer diameter ratio) greater than the ratio between the wall thickness of the tubular body 41 (e.g., including the liner 51, braiding 53 and the jacket 53) and the outer diameter of the guide catheter 40. In some embodiments, the first inflation tube 61 and the second inflation tube 62 can be less likely to kink compared to the tubular body 41 because of the higher wall thickness-to-outer diameter ratio. In some embodiments, a ratio between the outer diameter of the first inflation tube 61 (or the second inflation tube 62) and the outer diameter of the tubular body 41 (i.e. an inflation tube outer diameter-to-guide catheter outer diameter ratio) is less than about 0.15.

In some embodiments, as discussed herein, the first and second inflation tubes 61, 62 can be formed of a third type of polymer material. In some embodiments, the third type of polymer material of the first inflation tube 61 and the second inflation tube 62 can have relatively low tack, leading to instances where the inflation tube lumens can be more likely to unstick or not stick upon lumen collapse.

In some embodiments, the first inflation tube 61 and the second inflation tube 62 can be fused together to be part of a common elongated structure. In some embodiments, the first inflation tube 61 and the second inflation tube 62 can have an oval outer profile. In some cases, the inflation lumen of the first inflation tube 61 and the inflation lumen of the second inflation tube 62 have an oval inner profile. An oval profile, as compared to a circular profile, can minimize the height that the first inflation tube 61 and the second inflation tube 62 would add to the outer profile of the tubular body 41.

Figure 5:
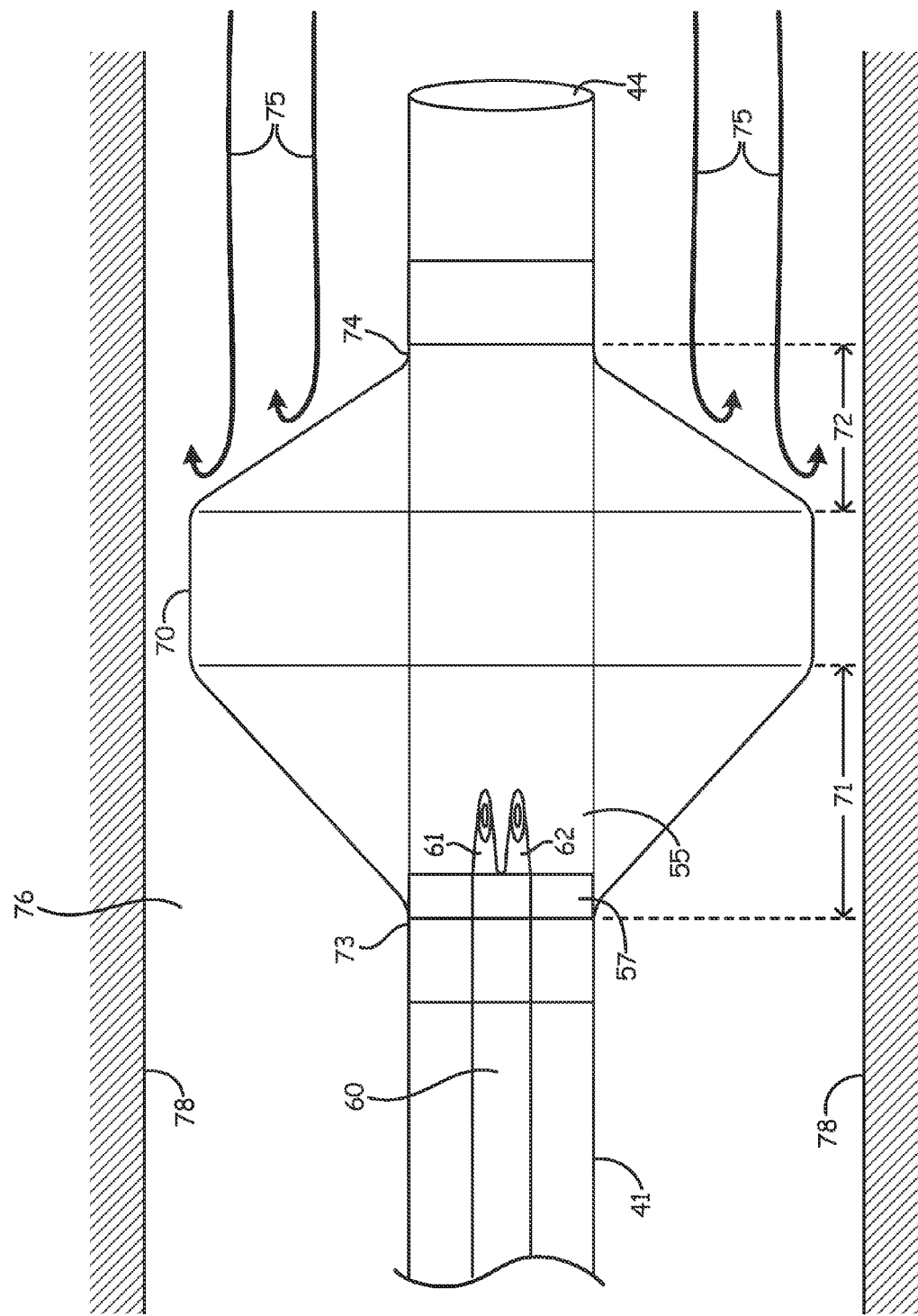
FIG. 5 illustrates a balloon on a guide catheter.

FIG. 5 is a schematic diagram of the balloon 70 inflated within a vessel 76 to at least partially occlude the vessel 76. The vessel 76 may correspond to the coronary sinus 31. As shown in FIG. 5, the balloon 70 is not expanded to the vessel wall 78. In various embodiments, the balloon 70 can be sized to expand to the vessel wall 78 to completely occlude the coronary sinus 31. As shown in FIG. 5, the pitch of the distal end profile 72 (i.e. the distal face) of the balloon 70 is steeper than the pitch of the proximal end profile 71 (i.e. the proximal face) of the balloon 70 when inflated, leading to a blunt profile and a tapered profile.

Flow lines 75 indicate the direction of blood flow within the vessel 76. Flow lines 75 further show that the blood flow can be redirected and/or become turbulent as the blood approaches the distal end profile 72 of the balloon 70. The blunt profile of the distal end profile 72 can be more likely to disrupt the laminar flow of blood which might otherwise easily flow around the balloon 70. As such, even though the balloon 70 may not fully occlude the vessel 76, the redirection and/or turbulent blood flow resulting from the blunt profile of the distal end profile 72 is more likely to allow injected contrast media to overcome the retrograde blood flow in the vessel 76 and reach branching vessels.

The relatively tapered profile of the proximal end profile 71 of the balloon 70 can facilitate smooth withdrawal of the balloon 70 into an outer catheter, such as an introducer (not illustrated). For example, the tapered profile of the proximal end profile 71 can minimize a retraction force necessary to pull the balloon 70 into a sheath when the balloon 70 is at least partially inflated. Also, the tapered profile of the proximal end profile 71 can be less likely to snag if the guide catheter 40 were to be withdrawn into an outer catheter.

In some embodiments, the balloon 70 can be pre-formed from fully compliant, semi-compliant, or non-compliant polymer material. In various embodiments, the balloon can be formed from a urethane material, a PEBA material, or a silicone material. Forming the balloon 70 from semi-compliant or non-compliant polymer material can allow the balloon 70 to have a different proximal end profile 71 and a different distal end profile 72 profile when the balloon 70 is inflated. The tapered and blunt profiles of the proximal end profile 71 and the distal end profile 72 can be formed from a heat mold having shapes corresponding to the tapered and blunt profiles.

The balloon 70 can include a proximal tail 73 and a distal tail 74. The proximal tail 73 and the distal tail 74 can be adhered to the tubular body 41 to seal the interior of the balloon 70 and permit the balloon 70 to hold pressure. The proximal tail 73 and the distal tail 74 can be bonded to the tubular body 41 by heat bonds or application of adhesive between the exterior surfaces of the tubular body 41 and the inner surfaces of the proximal tail 73 and the distal tail 74. Various shapes of the distal end profile 72 can be supported depending on the distance between the proximal tail 73 and the distal tail 74. For example, if the locations at which the proximal tail 73 and the distal tail 74 are bonded to the tubular body 41 are brought closer together, then the distal end profile 72 profile can form a puckered shape which can disrupt the retrograde blood flow of the vessel 76.

In some embodiments, the proximal tail 73 can be bonded to the tubular body 41 to overlap the bump 60. The inflation tubes 61 and 62 can emerge distally from the bump 60 and allow access to the interior of the balloon 70. As shown in FIG. 5, the second layer 57 can terminate underneath the balloon 70 distally of the proximal tail 73 and proximally of the distal tail 74. The first layer 55 can extend distally of the second layer 57 and distally of both the proximal tail 73 and the distal tail 74. The bump 60 can terminate underneath the balloon 70. The bump 60 can terminate at the distal terminus of the second layer 57. In some other embodiments, the second layer 57 extends distally of the distal tail 74. A lead can be advanced distally out of the distal opening 44 of the main lumen 50 into the vessel 76.

Figure 6:
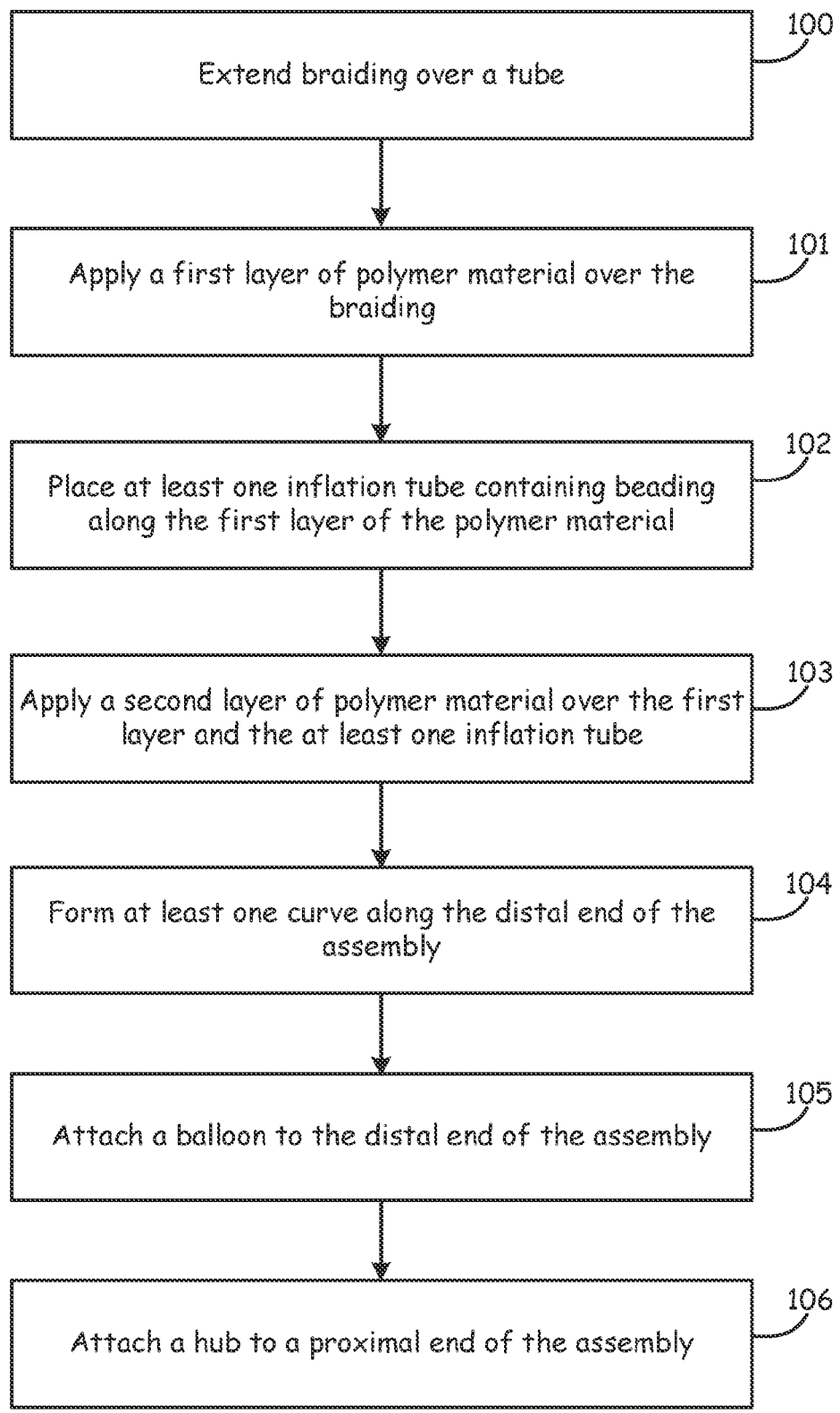
FIG. 6 illustrates a flow chart of a method of making a guide catheter.

FIG. 6 illustrates a flow chart of a method of making a guide catheter. The method can be used to make the guide catheter 40 of FIGS. 2-5. The method can include extending 100 braiding over a tube. In some embodiments, the tube can be placed over a mandrel to provide rigidity to the tube before the braiding is extended 100 over the tube. The tube can correspond to the liner 51. The tube can have a main lumen dimensioned to allow passage of a lead. The tube can be formed from a first type of polymer material. The braiding extended 100 over the tube can correspond to braiding 54. The braiding can be pre-wound into a sleeve that can be placed over the tube and then pulled on both proximal and distal ends of the braiding to fit the braiding over the tube.

The method can further comprise applying 101 a first layer of polymer material over the braiding. In some embodiments, the first layer of polymer material can be made from a second type of polymer material. Applying the first layer can comprise placing a tube of the second type of polymer material over the braiding and then placing a heat shrink tube, such as fluorinated ethylene propylene (FEP) over the tube of the second type of polymer material and heating the heat shrink tube to have the second type of polymer material flow over and within the braiding to form the first layer. The heat shrink tube can then be removed to expose the first layer. In some alternative embodiments, the first layer can be extruded over the braiding.

The method can further include placing at least one inflation tube containing beading along the first layer of the polymer material 102. The breading can extend entirely through the inflation tube such that the beading extends beyond the proximal and distal openings of the inflation tube. The beading can be made from PTFE or FEP, for example. The beading can have a circular cross section. In some embodiments, the beading has an outer diameter of about 0.003-0.006 inches. The beading can maintain the lumen of each of the at least one inflation tube during the subsequent processing steps.

Each of the at least one inflation tube can be formed from a third type of polymer material. In some embodiments, the third type of polymer material is the same as the first type of polymer material. The at least one inflation tube can correspond to the first inflation tube 61 and the second inflation tube 62, however a greater number of inflation tubes can also be placed 102 along the first layer. In some cases where multiple inflation tubes are placed 102 along the first layer, the multiple inflation tubes can be fused together (e.g., along the sides of the inflation tubes) to form a single elongate structure with separate lumens. The single elongate structure may be easier to handle and place 102 as compared to multiple tubes that are not connected to each other.

The method can further include applying 103 a second layer of polymer material over the first layer and each of the at least one inflation tube. The second layer of polymer can comprise a tube that has an inner diameter large enough to fit over the at least one inflation tube first extending along the first layer. A shrink tube can then be placed over the tube of the second layer (e.g., a FEP tube larger than the tube of the second layer) and heated to force the tube of the second layer to melt over and flow with the first layer. The polymer material of the second layer can be the second type of polymer material such that the first and second layers can melt and bond together to form a jacket of continuous polymer surrounding the braiding and within which are embedded the at least one inflation tube. The second layer can alternatively be applied 103 by extruding the second type of polymer material over the first layer and the at least one inflation tube. In some embodiments, the second layer is applied 103 distally of the distal end of the at least one inflation tube. In such a case, a hole can be drilled though the second layer to access the lumen of the inflation tube.

In some embodiments, the third type of polymer material can have a melting temperature that is higher than the melting temperature of the second type of polymer material. The second layer can be applied 103 by heating the material of the second layer to a temperature about equal to the melting temperature of the second type of polymer material but below the melting temperature of the third type of polymer material. The third type of polymer material having a melting point higher than the second type of polymer material can provide several advantages. First, the integrity of the inflation tube and the inflation lumen therein is maintained as the second type of material of the first and second layers is heated to melt and reflow. If the third type of polymer material melted at or below the melting temperature of the second type of polymer material (or if the assembly was heated to the melting temperature of the third type of polymer material), then the third type of polymer material may flow into the second type of polymer material and the inflation lumen may no longer be defined entirely by the third type of polymer material. As discussed herein, having each inflation tube be defined by a material different than the jacket material can provide several advantages, including resisting kinking while bending and collapsing under a vacuum.

PTFE can be suitable as the third type of polymer material for forming the inflation tube. However, PTFE ordinarily will not bond to most other materials, such as the second type of material forming the jacket. However, the exterior surface of the inflation tube can be chemically etched such that the second type of polymer material can melt around, and bond to, the exterior surface of each inflation tube. The chemical etching can also prevent each inflation tube from being exposed on the exterior surface of the guide catheter. In various embodiments, the second layer can be thin and unless the polymer material of the second layer bonds to the exterior of the inflation tube, the second type of polymer material may flow around the at least one inflation tube and expose the at least one inflation tube on the exterior of the tubular body. Accordingly, the chemical etching of the exterior surface of each inflation tube can ensure that the circumferential exterior surface of the tubular body is defined by the second layer and not the inflation tube.

The method can further include forming 104 at least one curve along the distal end of the assembly (e.g., the assembly at this stage comprising the second layer joined with the first layer and embedding the at least one inflation tube, wherein the braiding and the tube are covered by the first layer). The at least one curve can be heat set by bending the assembly to a desired shape and then heating the jacket to a temperature about equal to the melting temperature of the second type of polymer material but below the melting temperature of the third type of polymer material.

The method can further include attaching 105 a balloon to the distal end of the assembly. The balloon can be the balloon 70 illustrated and described herein. In some cases, a proximal tail of the balloon can be heat bonded to the assembly (e.g., the tail can be heated to bond to the second layer) before the distal tail of the balloon is also heat bonded to the assembly. However, after the proximal tail is attached, and before the distal tail is attached to the tubular body, the beading can be removed from each of the inflation tube. In this way, each of the processing steps involving significant heating that could affect the integrity of the inflation lumen can be complete (e.g., the applying 103 and forming 104 steps) such that the beading can be removed from the inflation tubes. In some cases, the beading can be stretched by pulling on both the proximal and distal ends of the beading simultaneously to draw down the profile of the beading to facilitate the removal of the beading. PTFE beading may be easier to remove relative to other materials because the PTFE material is unlikely to adhere to the third type of material of the inflation tubes during the preceding steps involving heating. Furthermore, ensuring that none of the preceding heating steps heat the third type of polymer material forming the at least one inflation tube to the melting temperature of the third type of polymer material can help avoid bonding between the beading and the at least one inflation tube. It is noted that it may be preferable to form 104 the at least one curve before attaching 105 the balloon because the balloon may straddle one of the curves and the process of heat setting a curve could melt the balloon.

The method can further include attaching 106 a hub to the proximal end of the assembly. The hub can be the hub 45 of FIG. 2. The hub can be attached 106 with a heat weld, a medical adhesive, or a solvent bond, among other attachment options. The hub can include an access port to the main lumen of the tubular body. The hub can include a single inflation port that is in communication with the at least one inflation tube (e.g., two or more inflation tubes), where the inflation port branches to each of the inflation tubes. The hub can include a port for the introduction of contrast media into the main lumen.

Figure 7:
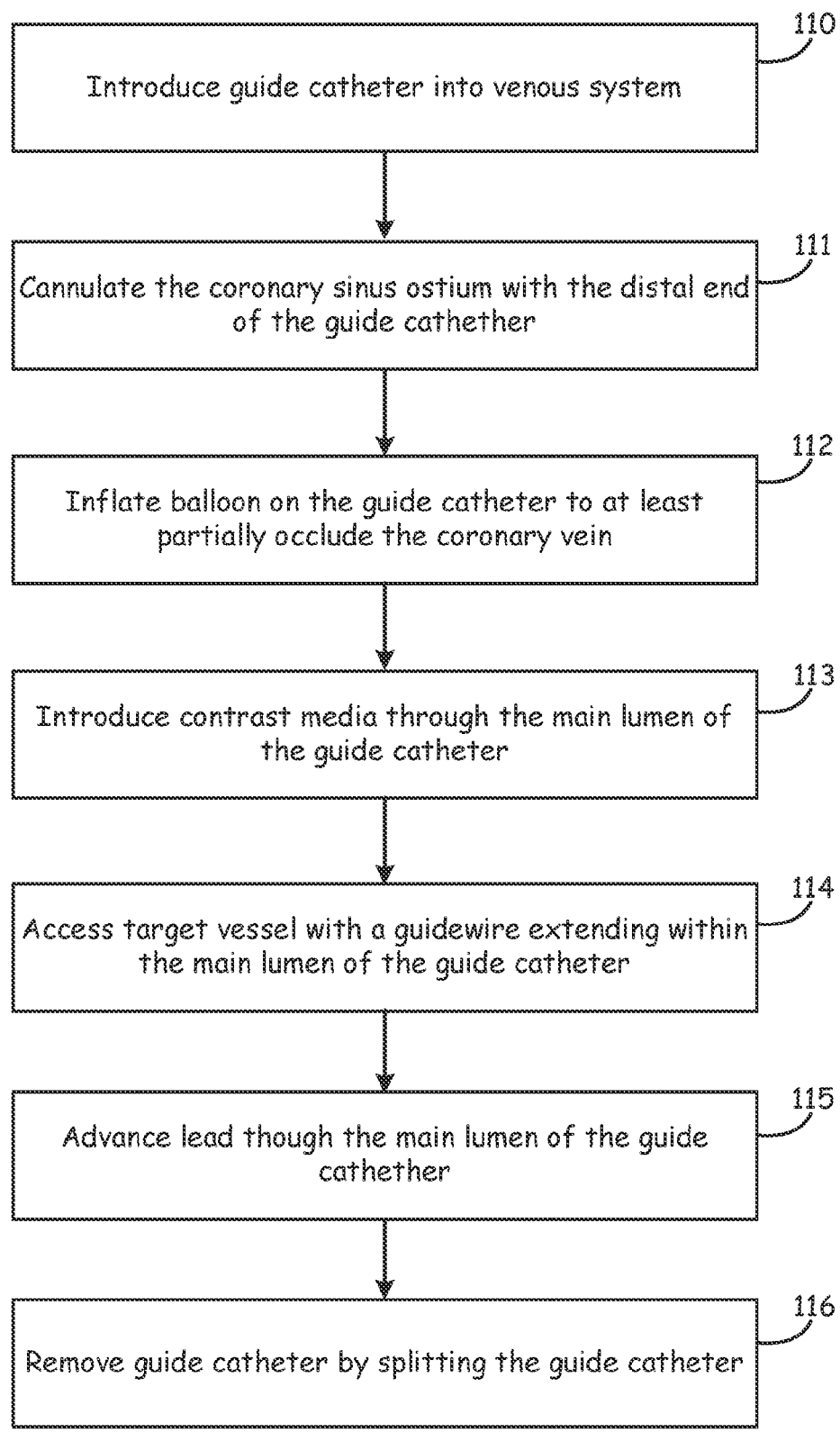
FIG. 7 illustrates a flow chart of a method of implanting a lead with a guide catheter.

FIG. 7 shows a flowchart of a method for implanting a lead with a guide catheter. The method can be performed using the guide catheter 40 of FIGS. 2 and 3, for example. The method can include introducing 110 a guide catheter into the venous system. The guide catheter can be introduced 110 into the venous system through a vascular entry site formed in the wall of the left subclavian vein or other vessel. In some cases, the guide catheter can be advanced through the left brachiocephalic vein and the superior vena cava to the right atrium. From the right atrium, the coronary sinus can be cannulated 111 by the distal end of the guide catheter. The balloon of the guide catheter can then be inflated 112 to at least partially occlude the coronary sinus. In various embodiments, the balloon can be inflated with air and not a fluid as the hydraulic pressure needed to inflate the balloon via the at least one inflation lumen of the at least one inflation tube (that may be particularly small to minimize the outer profile of the guide catheter) may be too high for the components of the guide catheter to handle and/or too high for a user to reasonably develop. With the retrograde blood flow of the coronary sinus at least partially blocked, contrast media (e.g., radiographic dye) can be introduced 113 into the coronary sinus through the main lumen of the guide catheter.

In some embodiments, a guide wire can be inserted through the hub and main lumen of the guide catheter to extend within the coronary sinus. Based on the vasculature revealed by the introduction 113 of the contrast media, a target vessel can be identified and the guide wire can access 114 the target vessel. The introduction 113 of contrast media can be repeated as necessary as the distal end of the guide wire is navigated through the vasculature.

With the guide wire accessing 114 a target vessel, a lead can be advanced 115 within the guide catheter over the guide wire. The lead can follow the guide wire to the target vessel. Once the lead is in place at the target vessel, the guide catheter can be removed 116 from over the lead. In some embodiments, the lead has one or more features which can allow the guide catheter to be split apart such that the guide catheter can be removed while leaving the lead in place. For example, the hub of the guide catheter can have a guide for directing a blade through a relatively thin and easily cut section of the hub. The guide can further direct the blade into and along the tubular body of the guide catheter.

Although exemplary embodiments presented herein concern a guide catheter for delivering a lead to the coronary sinus, the devices and methods can be applied to delivery of a lead to various other locations in the body. Although exemplary embodiments presented herein concern a guide catheter for delivering a lead, the features and methods can be applied to a catheter having a balloon and one or more inflation tubes (e.g., which may not involve delivery of a lead). Such a catheter can be configured for delivering one or more other elongated elements in the body.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A guide catheter for delivery of an implantable lead, the guide catheter comprising:
   a tubular body having a proximal end, a distal end, and a main lumen that extends from the proximal end to the distal end, the main lumen dimensioned to allow the implantable lead to move within the main lumen, the tubular body comprising:
      a jacket defining an exterior surface of the tubular body; and
      a plurality of inflation tubes embedded within the jacket;
      wherein an outer circumferential profile of the tubular body has a bump and the plurality of inflation tubes extend underneath the bump along the tubular body;
   a balloon mounted on the distal end of the tubular body, each of the plurality of inflation tubes in communication with the balloon, the balloon inflatable to at least partially occlude the coronary vein of the heart; and
   a hub mounted on the proximal end of the tubular body, the hub providing access to the main lumen and the plurality of inflation tubes.

2. The guide catheter of claim 1, wherein:
   an inner surface of the main lumen is defined by a liner formed from a first type of polymer material, and
   the jacket is formed from a second type of polymer material.

3. The guide catheter of claim 2, wherein:
   the tubular body further comprises a braiding circumferentially surrounding the liner, and
   the braiding is covered by the jacket.

4. The guide catheter of claim 2, wherein:
   the plurality of inflation tubes are formed from a third type of polymer material, and
   the second type of polymer material is different than the third type of polymer material.

5. The guide catheter of claim 4, wherein the third type of polymer material has a higher melting temperature than the second type of polymer material.

6. The guide catheter of claim 4, wherein the jacket comprises:
   a first layer of the second type of polymer material underneath the plurality of inflation tubes, and
   a second layer of the second type of polymer material disposed radially over the plurality of inflation tubes and bonded to the first layer.

7. The guide catheter of claim 1, wherein the plurality of inflation tubes extend adjacent to one another along the tubular body.

8. The guide catheter of claim 1, wherein the plurality of inflation tubes have greater kink resistance than the tubular body.

9. The guide catheter of claim 1, wherein the balloon has a blunted distal end profile when inflated that deflects retrograde blood flow in the coronary vein and a tapered proximal end profile that minimizes a retraction force necessary to pull the balloon into a sheath when the balloon is at least partially inflated.

10. A guide catheter for delivery of an implantable lead, the guide catheter comprising:
   a tubular body having a proximal end, a distal end, a main lumen that extends from the proximal end to the distal end, and an outer cross-sectional profile, the main lumen dimensioned to allow the implantable lead to move within the main lumen, the tubular body comprising:
      a liner defining an inner surface of the main lumen, the liner formed from a first type of polymer material;
      a jacket defining an exterior surface of the tubular body, the jacket formed from a second type of polymer material, the jacking including:
         a first layer of the second type of polymer material; and
         a second layer of the second type of polymer material disposed radially over the first layer; and
      at least one inflation tube embedded within the jacket, the at least one inflation tube extending from the proximal end to the distal end, the at least one inflation tube formed from a third type of polymer material, wherein each of the at least one inflation tube is more kink resistant than the tubular body, the second type of polymer material is different than the third type of polymer material, the outer cross-sectional profile of the tubular body has a bump that extends over the at least one inflation tube along the tubular body, the first layer extends underneath the at least one inflation tube, the second layer is disposed radially over the at least one inflation tube and bonded to the first layer, and the bump in the outer cross-sectional profile of the tubular body is at least partially formed by the second layer; and a balloon mounted on the distal end of the tubular body, the at least one inflation tube in communication with the balloon, the balloon inflatable to at least partially occlude the coronary vein of the heart.

11. The guide catheter of claim 10, wherein the balloon has a blunted distal end profile when inflated that deflects retrograde blood flow in the coronary vein and a tapered proximal end profile that minimizes a retraction force necessary to pull the balloon into a sheath when the balloon is at least partially inflated.

12. The guide catheter of claim 10, wherein each of the at least one inflation tube is more kink resistant than the tubular body based at least in part on the at least one inflation tube having a higher elongation characteristic than the tubular body.

* * * * *